(12) United States Patent
Henon

(10) Patent No.: US 10,302,242 B2
(45) Date of Patent: May 28, 2019

(54) DEVICE FOR POSITIONING AN OBJECT IN SPACE

(71) Applicant: HORIBA ABX SAS, Montpellier (FR)

(72) Inventor: Nathalie Henon, Fons (FR)

(73) Assignee: HORIBA ABX SAS, Montpellier (FR)

( * ) Notice: Subject to any disclaimer, the term of this patent is extended or adjusted under 35 U.S.C. 154(b) by 1078 days.

(21) Appl. No.: 14/386,964

(22) PCT Filed: Mar. 14, 2013

(86) PCT No.: PCT/FR2013/050533
§ 371 (c)(1),
(2) Date: Sep. 22, 2014

(87) PCT Pub. No.: WO2013/140068
PCT Pub. Date: Sep. 26, 2013

(65) Prior Publication Data
US 2015/0060614 A1 Mar. 5, 2015

(30) Foreign Application Priority Data

Mar. 22, 2012 (FR) ...................................... 12 52584

(51) Int. Cl.
*G01B 5/00* (2006.01)
*F16M 11/04* (2006.01)
*G01N 15/02* (2006.01)
*G01N 15/14* (2006.01)
*G01N 35/08* (2006.01)

(52) U.S. Cl.
CPC ......... *F16M 11/043* (2013.01); *G01B 5/0004* (2013.01); *G01N 15/0205* (2013.01); *G01N 15/1459* (2013.01); *G01N 35/085* (2013.01); *G01N 2015/149* (2013.01)

(58) Field of Classification Search
CPC ........ B23Q 1/282; B23Q 1/4852; B23Q 1/18; B23Q 1/4804; B23Q 1/626; Y10T 403/7096; Y10T 403/1616; Y10T 403/1624; Y10T 403/7094
USPC ........................................................ 248/122.1
See application file for complete search history.

(56) References Cited

U.S. PATENT DOCUMENTS 3,046,006 A * 7/1962 Kulicke, Jr. ........... B23Q 1/262
248/913
3,720,849 A 3/1973 Bardocz
(Continued)

FOREIGN PATENT DOCUMENTS

GB 550415 A 1/1943

OTHER PUBLICATIONS

International Search Report and Written Opinion of PCT/FR2013/050533 dated May 22, 2013.

*Primary Examiner* — Tyrone V Hall, Jr.
(74) *Attorney, Agent, or Firm* — Arent Fox LLP

(57) ABSTRACT

The subject of the invention is a device for positioning an object in space, comprising at least 4 plates, each one able to move with respect to another of said plates which is contiguous with it along one of the 3 axes of space, it being possible for the movement of one plate with respect to another plate to be guided by a tenon/mortise assembly in which said tenon is secured to one of the plates and its mortise is produced in the other plate, the spatial orientation of each of the tenon/mortise assemblies being different from the other 2 and along one of the 3 axes of space.

20 Claims, 4 Drawing Sheets

(56) References Cited

U.S. PATENT DOCUMENTS

| | | | | |
|---|---|---|---|---|
| 4,221,391 A * | 9/1980 | Dutton | ............ | B23B 31/16275 |
| | | | | 269/271 |
| 4,652,095 A * | 3/1987 | Mauro | ............... | G01B 5/0002 |
| | | | | 108/143 |
| 4,735,451 A * | 4/1988 | Wojciechowski | ..... | B25J 15/028 |
| | | | | 269/234 |
| 5,384,663 A * | 1/1995 | Garrett | ............... | B23Q 1/4804 |
| | | | | 359/874 |
| 5,547,330 A * | 8/1996 | Walimaa | ............. | F16M 11/043 |
| | | | | 269/71 |
| 5,551,795 A * | 9/1996 | Engibarov | .............. | B23Q 1/28 |
| | | | | 269/73 |
| 5,716,043 A * | 2/1998 | Iwata | ...................... | B23Q 1/28 |
| | | | | 269/73 |
| 6,139,001 A * | 10/2000 | Buck | ................... | B25B 1/2405 |
| | | | | 267/43 |
| 6,174,102 B1 * | 1/2001 | Do | ........................ | B23Q 1/282 |
| | | | | 269/71 |
| 2011/0036966 A1 * | 2/2011 | Benedict | ............... | E02D 27/02 |
| | | | | 249/25 |

\* cited by examiner

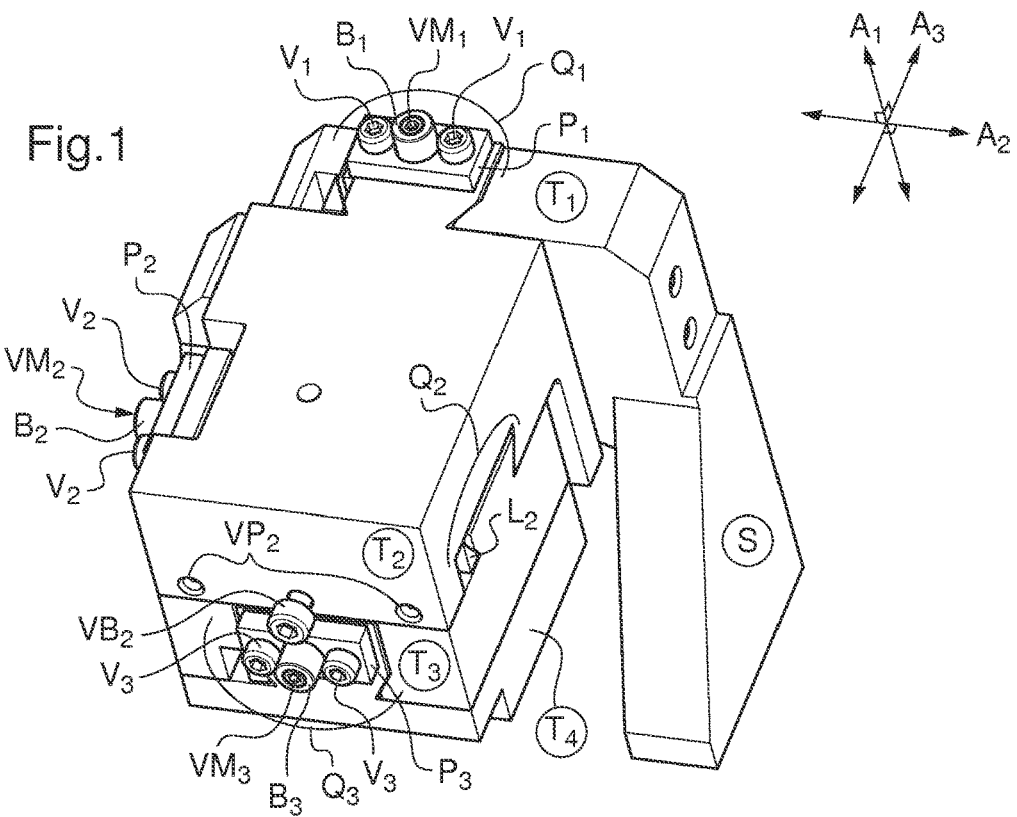
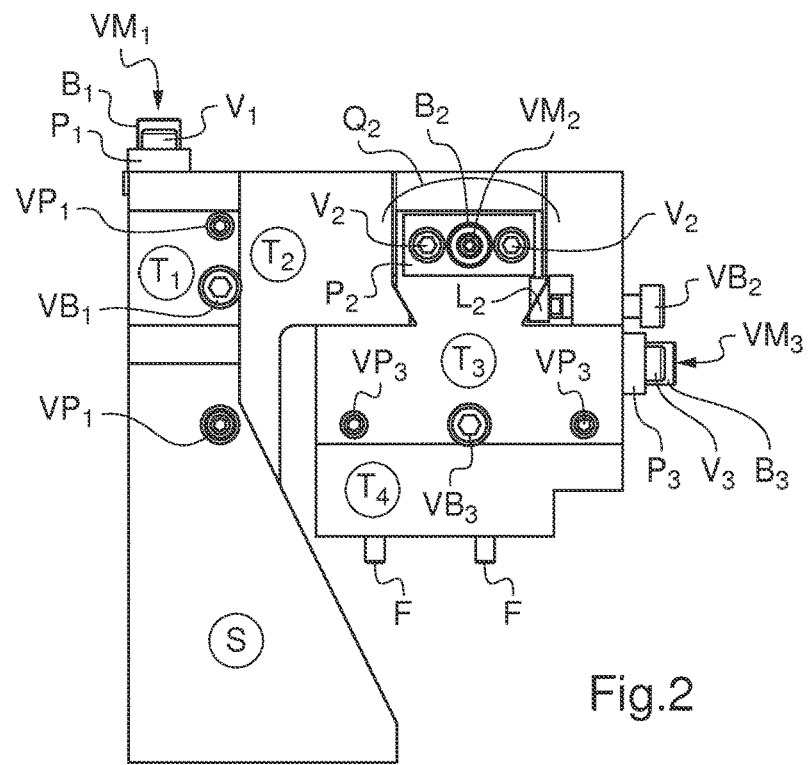

DEVICE FOR POSITIONING AN OBJECT IN SPACE

CROSS-REFERENCE TO RELATED APPLICATIONS

This application is the U.S. National Phase of International Patent Application No. PCT/FR2013/050533, filed Mar. 14, 2013, which claims priority to FR 1252584, filed Mar. 22, 2012, the contents of each are hereby incorporated by reference in their entireties.

The invention falls within the field of devices for positioning an object in space, more specifically within the field of devices for positioning an object in space with very high or micrometric precision, particularly those used in measurement apparatus such as those for example used in flow cytometry.

Flow cytometry is a technique that allows particles, molecules or cells, carried in a carrier fluid, to file past at high speed as far as a luminous excitation source, for example a light beam, advantageously the beam of a laser. This technique allows said particles, molecules or cells to be sorted and/or counted and/or characterized individually, quantitatively or qualitatively, notably by analyzing the optical and/or physical signals emitted by said particles, molecules or cells as they cross said luminous excitation source.

Said particles, molecules or cells for analysis are placed in single file in said carrier fluid using the principle of hydrodynamically focusing the carrier fluid, and are conveyed as far as the luminous excitation source. According to this principle, a sheath liquid channels said carrier fluid, this combined assembly flowing in the form of a laminar flow, guaranteeing that said carrier fluid does not mix with said sheath liquid. It will therefore be appreciated that the dimensions of said carrier fluid are extremely minimal.

The same is generally true of the dimensions of the beam of said luminous excitation source.

But the method works only if said beam from said luminous excitation source encounters said particles, molecules or cells that are to be analyzed.

It is therefore absolutely essential that the spatial positioning of said luminous excitation source and of said carrier fluid be as precise as possible so that the point at which the two converge is as fine as possible.

Likewise, it is necessary for there to be no chance of unwanted variation in positioning occurring during setup and/or measurement.

In general, in cytometry equipment, the position of said carrier fluid is fixed and it is the luminous excitation source that is moved around so that the radiation it produces is positioned very precisely at the center of the flow of carrier fluid.

The device according to the invention when used in cytometry equipment is therefore more particularly intended to position the luminous excitation source (generally laser radiation) relative to the flow of carrier fluid.

Devices for positioning an object in space are known from the prior art. However, without questioning their qualities, these devices are not entirely suited to the use to which the applicant company wishes to put them in measurement equipment, particularly micrometric measurement equipment, very specifically equipment used in flow cytometry.

Hence the applicant company found itself facing various problems that it sought to address through the present invention.

Specifically, the applicant company found itself needing to provide positioning to within one hundredth of a millimeter along the 3 axes of space while at the same time limiting operating clearances within one hundredth of a millimeter and keeping the entire device as firmly as possible held in the position defined by the operator during setup.

However, as with all devices of this type, it was also necessary to maintain a function of compensating for chance variations in movement, namely for compensating for the functional clearance associated with the movement, a function usually performed in known devices of the prior art using springs or balls.

It was additionally necessary to provide the entire device with a high level of dimensional stability in the event of variations in temperature thus minimizing variations in dimensions that are associated with expansion/contraction (differential expansion) phenomena caused by variations in temperature.

It was finally necessary to keep the device as a whole as compact as possible, guaranteeing the user a high level of precision in the movement in each of the three axes of space, giving the user maximum sensitivity and a very precise travel.

Precision in the context of movement here means that the device according to the invention must guarantee the user that when he repeats a predefined given movement on a movement means of one of the elements of said device according to the invention he always obtains an identical result. In the specific case of the invention, the action performed by the user, for example turning one of the movement means of one of the elements of said device according to the invention (for example a micrometer screw) through 10° (which is the maximum sensitivity generally accepted by a person skilled in the art in one direction or the other), must guarantee that said element moves through between 0.1 and 100 µm, preferably 2 and 50 µm, very preferably 5 µm.

Maximum sensitivity for the user means, according to the invention, that when the operator makes an adjustment to one of the movement means of one of the elements of said device according to the invention (for example a screw) he (or she) must be able to feel a movement of 10 µm.

Travel according to the invention means the maximum amplitude of movement available in the system for positioning the object in space, for example for targeting the firing of a laser in the case of cytometry measurements. For example, said travel along each axis may be between 0 and 10 mm, namely +/−5 mm on each side of the target position, advantageously between 0 and 6 mm, namely +/−3 mm either side of the target position.

The solution proposed by the applicant company lies in a device for the micrometric positioning of an object in space comprising just 4 plates each one able to move relative to another contiguous with it without intermediate components, said device being free of any system that compensates for chance variations in movement in the form of springs or balls as are present in the known devices from the prior art for the micrometric positioning of an object in space.

The reduced number of plates that make up the device (4 plates) seeks to solve the problem of keeping the device compact.

The absence of a spring also partly solves the problem of the dimensional stability of the said device as a whole in the event of variations in temperature as the springs cannot be made from the same material as the plates with the result that variations in temperature could have caused differences in expansion/contraction detrimental to the dimension stability of the device as a whole, especially in a micrometric device.

According to the invention the function of compensating for chance variations in movement is performed by the combination of a lateral preload applied to the means of guiding the movement of one plate relative to the other and the use of a micrometer screw intended to move one plate relative to another when turned, said micrometer screw being fixed in direct mesh with the plate that it moves.

Thus, one subject of the invention is a device for positioning an object in space, comprising at least 4 plates (T1, T2, T3, T4), each one able to move with respect to another of said plates which is contiguous with it along one of the 3 axes of space, it being possible for the movement of one plate with respect to another plate to be guided by a tenon/mortise assembly in which said tenon may be secured to one of the plates and its mortise may be produced in the other plate, the spatial orientation of each of the tenon/mortise assemblies being different from the other 2 and along one of the 3 axes of space characterized in that said device is free of any compensating spring at least one of the tenon/mortise assemblies may be in the form of a dovetail;

a preload aimed at limiting the movement of one plate with respect to another is applied laterally to one of the edges of the tenon of the tenon/mortise assembly, said preload limiting but not preventing the movement of said plates one relative to another;

the movement of at least one plate relative to another plate may be brought about by means of at least one micrometer screw able to act at least on one of the two plates that are to be moved one relative to the other, being possible for said micrometer screw to be secured to one of said two plates, and for said micrometer screw to be fixed in direct mesh with said plate;

one plate can be locked in the desired position relative to another plate independently for each of the tenon/mortise assemblies, using at least one locking means.

Fixed in direct mesh with the plate that it is to move means that the micrometer screw is secured without play to the plate that it moves by a means which, while providing a firm connection between the screw and the plate, leaves the micrometer screw free to turn. According to the invention, said means consists of a collar of cylindrical shape force-fitted onto one of the ends of said micrometer screw, advantageously as a press fit, having a body of given diameter and a base secured to said body having a given diameter greater than that of said body and thus forming a flange around said body. Advantageously, the collar is a single milled component, the body and the flange thus being one and the same component.

Said flange is intended to be housed in a circular recess of the same diameter and of a depth equal to the thickness of said flange, which is made in the plate that is to be guided. When said flange is positioned in the recess in the plate, the collar/micrometer screw assembly is secured to said plate by means of a bracket of any shape, advantageously rectangular, having an orifice of a diameter corresponding to the outside diameter of the body of the collar through which orifice said body of the collar passes, said bracket being fixed to said plate that the micrometer screw is to move. Any means of fixing said bracket to said plate can be used according to the invention, and said bracket may preferably be fixed to said plate using a screw, advantageously 2, each situated on either side of the orifice through which the body of the collar passes.

It will be appreciated that the micrometer screw and the collar, joined together, rotate together. It will also be understood that the collar/bracket assembly limits the undesired longitudinal play of said micrometer screw.

According to the invention, the micrometer screw may be such that turning its head by one complete revolution may move its end through a distance of between 0 and 1000 μm, preferably between 0 and 500 μm, very preferably 200 μm.

It has also been understood from the foregoing that two contiguous plates may move one relative to the other. For that, the two plates are connected to one another by a tenon/mortise assembly, said tenon being an integral part of one of the plates, said mortise being an integral part of the other plate. It is conceivable for said tenon to be an independent component attached to the plate but it is far more advantageous for said plate in fact to be made in a single piece that is machined, for example milled, in order to form said tenon.

It is also understood that the mortise part of the tenon/mortise assembly may be machined, advantageously milled, in the plate.

As indicated previously, at least one of the tenon/mortise assemblies is in the form of a dovetail. According to one alternative form of the invention, 2 of the tenon/mortise assemblies, but very preferably all 3, may be in the form of dovetails.

According to the invention, the dimensions of the tenon/mortise assembly will depend on the overall dimensions of the device and a person skilled in the art will have no trouble defining them. However, because the guidance and straightness of the movements of the tenons are performed by at least one of the edges of the mortises, advantageously both, it may be advantageous for the tenon/mortise assembly to be of the greatest possible length. That will also allow better distribution of forces, particularly the preload and/or locking forces. Advantageously according to the invention, the tenon/mortise assembly may be of a length equivalent to the length of the plate in which the mortise is milled.

It is also understood that the movement of one plate relative to another may be limited without being prevented by the application of a preload to the tenon of the tenon/mortise assembly connecting said 2 plates.

Said preload, advantageously set at the time of assembly of said device according to the invention, can be obtained according to the invention by a preloading means which, in a tenon/mortise assembly, will limit the movement of said tenon in its mortise, without in any way blocking the movement of said tenon in said mortise.

It is obvious that, according to the invention, one, several or all of the tenon/mortise assemblies may comprise said loading means. Advantageously according to the invention, all the tenon/mortise assemblies may comprise said preload means.

According to the invention, said preload means that is to preload the movement of a tenon in its mortise may be positioned tangentially to said tenon, over the greatest length of said tenon.

According to the invention, said preload means may be one of the edges of said mortise.

Because the movement of one plate relative to another is guided by a tenon/mortise assembly, the walls of said mortise perform the function of guiding the movement of said tenon. According to the invention, the mortise is advantageously milled in the mass of the plate. Advantageously, one of said walls of said mortise is therefore milled in the form of a blade that has a certain degree of lateral elasticity, said blade being secured to the plate in which the mortise of which it forms one of the edges is milled. Lateral elastically means that if a force is applied laterally to said blade and therefore at right angles to the direction of the guidance performed by said blade, said blade is able to move laterally without becoming detached from the plate, and therefore to adopt an angle of inclination with respect to its base. It is understood that when said force is applied, said blade becomes inclined and comes into contact with the wall of the tenon that it guides.

According to the invention, said blade performs two functions: first, it allows application of said preload aimed at limiting without eliminating the movement of a tenon in its mortise and second it allows the two contiguous plates to be locked when the desired position of one of the plates relative to the other is reached.

It is therefore understood that the device may comprise, on the one hand, a means for applying said preload force to said blade, advantageously at least one screw which is also referred to as the preload screw, positioned at right angles to the axis of movement of said tenon/mortise assembly to which said preload is to be applied and, on the other hand, a means of locking the position of one plate relative to the other, advantageously at least one screw moreover also referred to as a locking screw, likewise positioned at right angles to the axis of movement of said tenon/mortise assembly to which said locking is to be applied.

Advantageously according to the invention, the device may comprise 2 preload screws and one locking screw. The preload screws and the locking screw act on one and the same blade, one advantageous embodiment of the invention having the possibility of the two preload screws being situated one on each side of the locking screw. It will be understood that, according to the invention, each tenon/mortise assembly may comprise a preload screw and locking screw assembly.

One of the advantages of the preload/locking means according to the invention is that since said blade that applies the preload or the locking to the tenon extends over the entire length of the mortise, the loading and/or locking force applied is therefore applied over the entire length of the tenon to which it is applied, giving a better distribution of the applied forces. Another advantage is that since said blade is obtained by machining the plate, it happens to be made from the same material as said plate, thus contributing to addressing the problem of the dimensional stability of the device as a whole in the event of variations in temperature since the plate and said blade are made of the same material.

According to the invention a plate means a component the volume of which is defined by a length, a width and a height, in which the width and the length define a shape which may be a circle or a polygon, advantageously a square, a rectangle, or a triangle and at least two parallel faces of which are planar. Advantageously, according to the invention, the plate will be a square, rectangular or rhombohedral parallelepiped. According to the invention, the 4 plates may be of different shapes. Advantageously, the 4 plates may be of the same shape and/or size. Very advantageously, the 4 plates of the device according to the invention may be a rectangular parallelepiped the largest surface of which may be square. Furthermore, according to the invention, said plates, simultaneously or independently, may comprise fixing means intended to secure to said plates any object that the device according to the invention wishes to be able to position in space.

According to the invention, 3 of the 4 plates of the device may be stacked one on the next via their planar faces, it being possible for the fourth to be positioned on one of the two other faces of the volume defined by the stack of the other 3 plates. It will be understood that this fourth plate may comprise a mortise oriented along an axis parallel to the axis of stacking of the other 3 plates so that thanks to a tenon borne by one of the other 3 plates which are stacked and intended to fit into said mortise, all 3 stacked plates can be moved at the same time along the axis defined by the mortise borne by the said fourth plate.

According to the invention, the plates may be made of any material compatible with the intended use of the device. For preference, according to the invention, the material may be a substance which is as inert as possible in the face of temperature variations. For example, they may be made of aluminum, steel, advantageously stainless steel, brass, or hard plastic. The terms aluminum, steel, brass, hard plastic are used here as generic terms each denoting a family of products made available by the manufacturers and from which a person skilled in the art will have no difficulty selecting the product best suited to the manufacture of the device according to the invention to suit the manufacturing constraints that he may encounter.

Advantageously according to the invention, the material used in the majority will be aluminum.

Likewise, while it is conceivable for the plates to be made from different materials, it may be advantageous for all 4 plates of the device to be made from the same material. This is the preferred alternative form of the invention.

According to the invention, the tenons may also be made from any material compatible with the intended use of the device. Likewise, while it is conceivable for the various tenons to be made from different materials, it may be advantageous for all the tenons of the device to be made from the same material and more advantageous still for this material to be the same as the material from which said plates may be made. Advantageously, as each plate is machined in order to give it its definitive shape, the tenon of each plate will be made of the same material as said plate.

In fact, most of the components of which the device according to the invention is made may be made from the same material, advantageously aluminum, the purpose of this being to contribute to solving the problem of the dimensional stability of the said device as a whole in the event of temperature variations, as the plate and said blade are made from the same material. According to a particularly advantageous and preferred alternative form of the invention, only the screws (micrometer screws, differential pitch screws or other screws) will not be made from the same material as the other components (plates, flanges, brackets). As the device is therefore made of one single material, this form of embodiment guarantees the device as a whole very great stability in the face of temperature variations.

The dimensions of the device and/or of each component of said device are not in themselves an essential feature of the invention because the device according to the invention is intended to be used in apparatus which will itself introduce constraints as to the dimensions of said device according to the invention. A person skilled in the art will know perfectly well how to adapt the dimensions of the various components of said device according to the invention so that the latter has the desired dimensions for use in such or such an apparatus, and will be able to do so without difficulty.

Objects, features and advantages of the invention will become apparent from the following description, given by way of nonlimiting illustration, with reference to the attached drawings in which:

FIG. 1 shows a three-dimensional view of one alternative form of a device according to the invention.

FIG. 2 shows a side view of one alternative form of a device according to the invention.

FIG. 1 depicts a three-dimensional view of an alternative form of the device according to the invention, showing the 4 plates (T1, T2, T3 and T4) of the device and the dovetail tenon/mortise assembly (Q) that allows the plates T1 and T2 (Q1), T2 and T3 (Q2) and T3 and T4 (Q3) to move one relative to another.

It will be noted that for each tenon/mortise assembly there is a micrometer screw VM (VM1 for the assembly Q1, VM2 for the assembly Q2 and VM3 for the assembly Q3). Each of the micrometer screws VM is kept attached to the plate that bears it by a collar B (B1, B2 and B3) that is itself held in place by a bracket P (P1, P2, P3) itself held in place by 2 screws V (V1 for collar B1, V2 for collar B2, V3 for collar B3).

Of note, visible on the plate T2, is the locking screw (VB2) which acts on the tenon/mortise assembly Q2 (the locking screws VB1 and VB3 acting on the tenon/mortise assemblies Q1 and Q3 are not visible in the figure).

Finally of note, likewise visible on the plate T2, are 2 preload screws (VP2) which apply a preload to the tenon of the tenon/mortise assembly Q2 (the preload screws VP1 and VP3 acting on the tenon/mortise assemblies Q1 and Q3 are not visible in the figure).

Also of note and visible on the plate T2 is the blade L2 via which the preload and the locking of the tenon/mortise assembly Q2 is applied when the preload force is created by the preload screws VP2 and the locking force is created by the locking screw VB2.

In FIG. 1, the device according to the invention is held in a support (S) via the plate T1.

It will be understood by studying FIG. 1 that the plate T2 can move relative to the plate T1 along the axis A1 by means of Q1 and VM1, that the plate T3 can move relative to the plate T2 along the axis A2 by means of Q2 and VM2, that the plate T4 can move relative to the plate T3 along the axis A3 by means of Q3 and VM3, each axis being in a plane perpendicular to the planes in which the other 2 axes lie.

FIG. 2 is a side view of the device according to the invention of FIG. 1, and shows the 4 plates of the device (T1, T2, T3 and T4), the dovetail tenon/mortise assembly allowing the plate T3 to move relative to the plate T2 (Q2), the micrometer screws VM1, VM2 and VM3, the collars B1, B2 and B3, the locking screws VB1, VB2 and VB3, the preload screws VP1 and VP3 (the preload screws VP2 not being depicted), and the brackets P1, P2 and P3. Note the presence of screws V1, V2 and V3 which are used to hold the brackets P1, P2 and P3.

Also of note is the presence of the blade L2 secured to plate T2 and via which the preloading and locking of the tenon/mortise assembly Q2 is had when the preload force is applied by the preload screws VP2 (not depicted) and the locking force is applied by the locking screw VB2.

Also depicted are the support S and, under the plate T4, two object-fixing means (F).

Figure 3A:
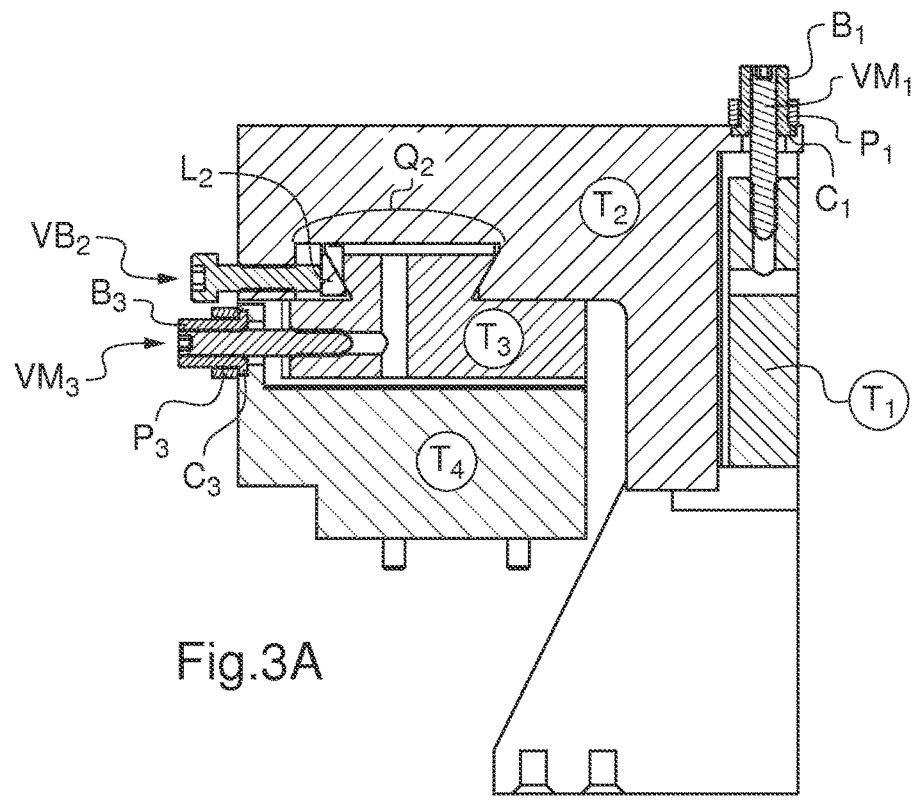
FIG. 3 shows at A a cross section through a device according to the invention and at B an enlargement of the locking means and of the movement means that lock and move one of the plates of said device.

FIG. 3A depicts a cross section of the device according to the invention and shows the plates T1, T2, T3 and T4, the micrometer screws VM1 and VM3, the locking screw VB2, the dovetail tenon/mortise assembly Q2, the collars B1 and B3 and the brackets P1 and P3.

Also of note are the presence of the blade L2 secured to the plate T2, via which blade the preload and locking of the tenon/mortise assembly Q2 is achieved when the preload force is created by the preload screws VP2 (not depicted) and the locking force is created by the locking screw VB2.

Figure 3B:
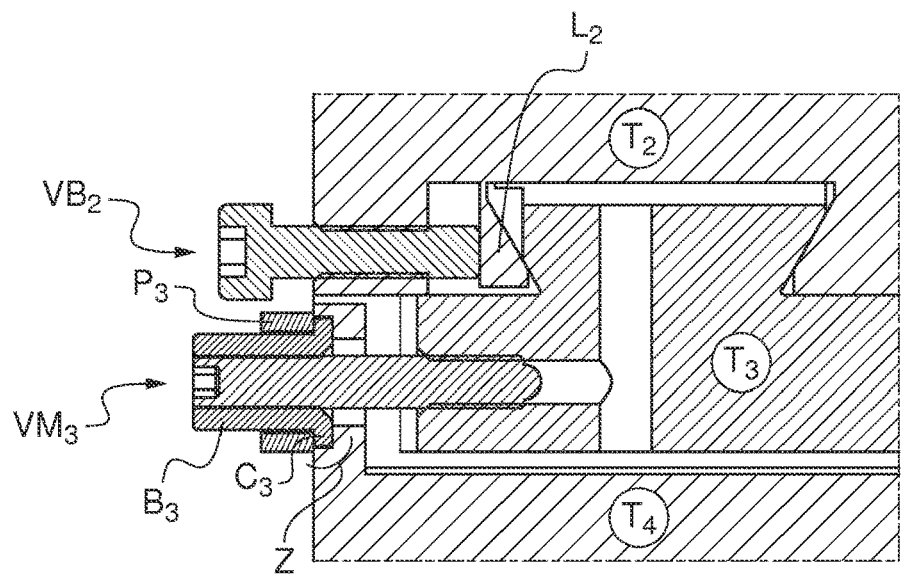

FIG. 3B is an enlargement showing the locking screw VB2 and the micrometer screw VM3.

Note that the locking screw VB2 acts on the blade L2 secured to the plate T2 so that said blade L2 can rub against the chamfered edge of the tenon of the plate T3. This is how the plate T2/plate T3 assembly is locked in the desired position.

The micrometer screw VM3 is secured to the plate T4 by the collar B3 the flange-shaped base C3 of which is, on the one hand, inserted in a housing of the same size formed in T4 (E), the VM3/B3 assembly being secured to T4 by the bracket P3.

It will be understood from studying FIG. 3B that turning the VM3/B3 assembly causes the plate T4 to move relative to the plate T3 by microscrewing into said plate T3.

Figure 4:
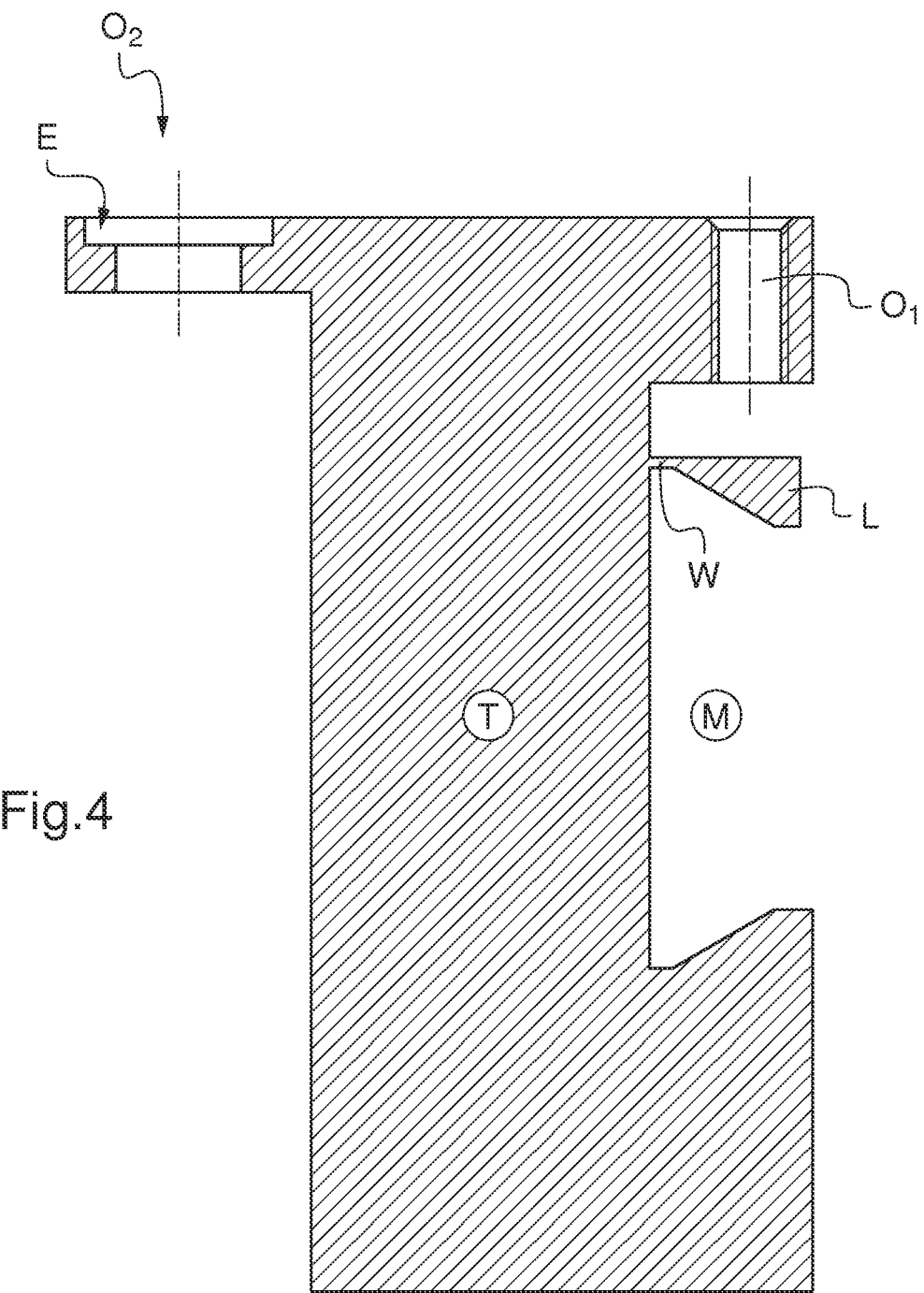
FIG. 4 is a cross section through a plate.

FIG. 4 shows a cross section through a plate on a plane perpendicular to the axis of the mortise borne by said plate.

This cross section shows the plate T, the dovetail mortise M, the blade L of the preload/locking means secured to the plate T by its base W, the orifice O1 through which there passes the locking screw that applies the locking force that locks the tenon/mortise assembly M via the blade L, the orifice O2 through which there passes the micrometer screw that moves the plate T3 in which can be seen the recess E intended to house a flange C of a collar B secured to the micrometer screw VM passing through the orifice O2.

FIG. 5 depicts an exploded three-dimensional view of a device according to the invention (5A) and an enlargement (5B) of the micrometer screw (VM), collar (B), bracket (P) assembly in position on a lateral wall of a plate T.

Figures 5A, 5B:
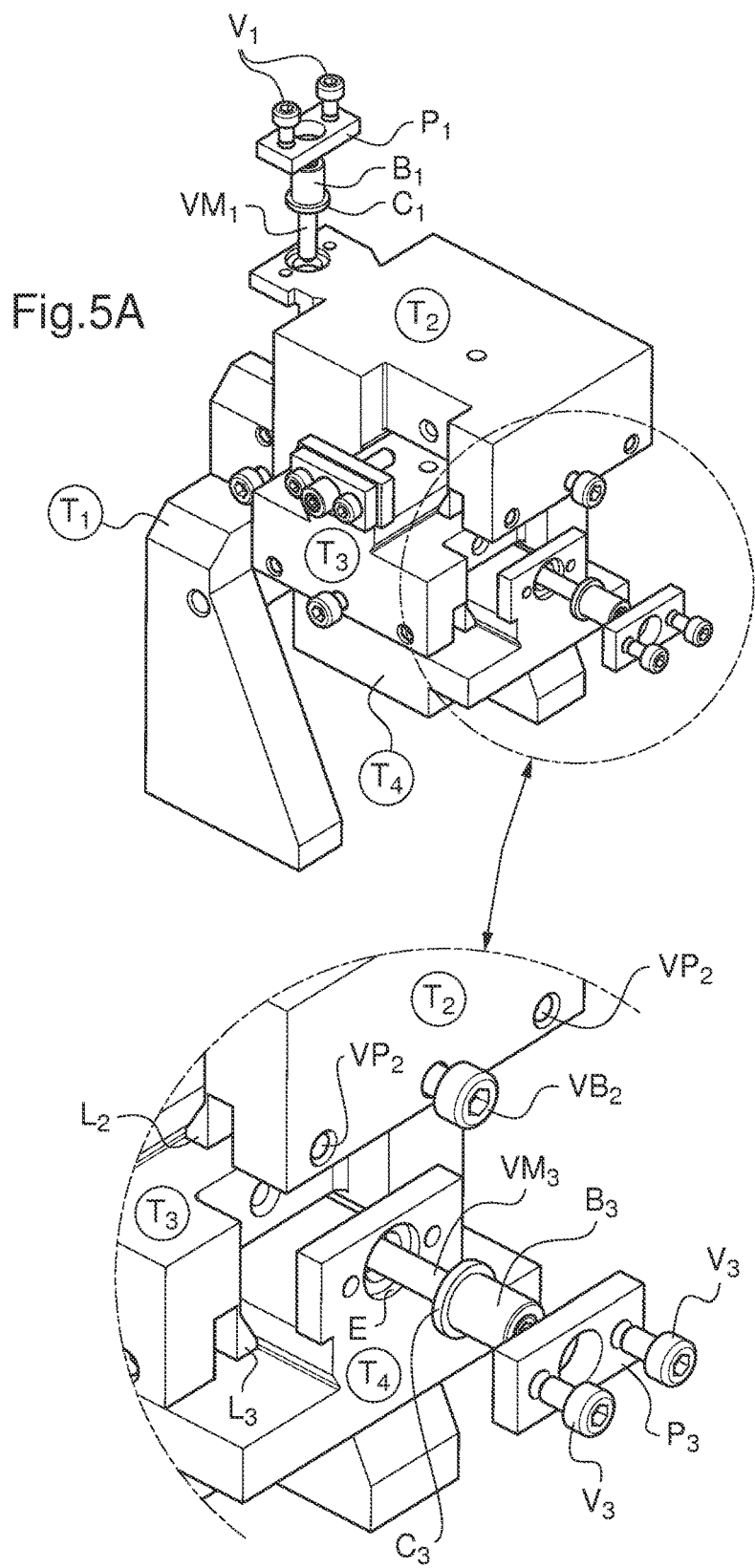
FIG. 5 is an exploded three-dimensional view of how the micrometer screw/flange/bracket assembly is mounted on a plate to fix said micrometer screw in direct engagement with said plate.

FIG. 5A shows the plates T1, T2, T3 and T4. The figure shows, for the plate T2, how the micrometer screw VM1 intended to move the plate T2 relative to the plate T1 is mounted. Note the depiction of the micrometer screw VM1, of the collar B1 and of its flange C1, and the bracket P1 intended to hold the micrometer screw VM1, collar B1 and flange C1 assembly fixed to the plate T2 using the screws V1.

FIG. 5B is an enlargement of how the micrometer screw VM3 intended to move the plate T4 relative to the plate T3 is mounted. Note on the plate T4 the recess E intended to accept the flange C3 secured to the collar B3 pressed onto the micrometer screw VM3. Note too the bracket P3 intended to fix in direct engagement the micrometer screw VM3, collar B3 and flange C3 assembly that is fixed to the plate T4 using the screws V3.

The figure also shows the plates T2 and T3 and the locking screw VB2 intended to lock the plate T3 in the desired position relative to T2 and the location of the preload screws VP2 intended to apply the desired preload to the plate T3. Note the depiction of the blade L2 on which the preload screws VP2 and the locking screw VB2 act so as to preload and block the movements of the plate T3 relative to the plate T2. Likewise, the blade L3 on which the preload screws VP3 and the locking screw VB3 (none of which are depicted) act in order to preload and block the movements of the plate T4 relative to the plate T3.

The invention claimed is:

1. A device for positioning an object in space, comprising at least 4 plates, each one of said plates being movable with respect to another of said plates such that at each plate is contiguous with another of said plates along one of 3 axes of space, each of said plates further comprises at least one of a tenon/mortise assembly which guides the movement of at least one plate with respect to at least another plate, wherein the tenon is on one of the plates and the mortise is on the other plate, the spatial orientation of each of the tenon/mortise assemblies being different from the other 2 and along one of the 3 axes of space wherein:
   said device is free of any compensating spring;
   at least one of the tenon/mortise assemblies is in the form of a dovetail;
   a preload member configured to apply a lateral preload to one of the edges of the tenon of the tenon/mortise assembly, said preload member comprising a blade having a distal end and a proximal end that is narrower than the distal end, wherein the preload member is configured to limit but not prevent the movement of said plates relative to another;
   at least one plate is movable relative to another by at least one micrometer screw acting on at least one of the two plates that are to be moved relative to the other, said micrometer screw being secured to a first one of said two plates, said micrometer screw being fixed in direct mesh with a second one of said two plates and is free to turn, wherein the micrometer screw is secured with a collar of cylindrical shape force-fitted onto one of the ends of said micrometer screw, and of a bracket, having an orifice of a diameter corresponding to the outside diameter of a body of the collar through which orifice said body of said collar passes, said bracket being fixed to the plate that the micrometer screw is to move;
   at least one plate of the at least 4 plates is capable of being locked in the desired position relative to another plate of the at least 4 plates, wherein said plate is locked independently of the tenon/mortise assemblies associated with the plate.

2. The device according to claim 1, wherein at least 2 of the tenon/mortise assemblies are in the form of dovetails.

3. The device according to claim 2, wherein 3 of the tenon/mortise assemblies are in the form of dovetails.

4. The device according to claim 1, wherein the micrometer screw is configured so that turning its head by one complete revolution moves at least one of the first one and the second one of the two plates a distance of between 0 and 1000 µm with respect to the other of the first one and second one of the two plates.

5. The device according to claim 4, wherein turning the head by one complete revolution moves at least one of first one and second one of the two plates a distance of between 0 and 500 µm with respect to the other of the first and second one of the two plates.

6. The device according to claim 5, wherein turning the head by one complete revolution moves at least one of first one and second one of the two plates a distance 200 µm with respect to the other of the first and second one of the two plates.

7. The device according to claim 1, wherein said collar has a body of given diameter and a base secured to said body having a given diameter greater than that of said body and thus forming a flange around said body.

8. The device according to claim 1, wherein movement of one plate relative to another is limited without being prevented by the application of a preload, by the blade to the tenon of the tenon/mortise assembly connecting said two plates.

9. The device according to claim 8, wherein said preload member is one of the edges of said mortise.

10. The device according to claim 9, wherein said edge of said mortise is the blade, wherein the blade exhibits a lateral elasticity, wherein the blade is formed as a unitary structure with the plate associated with said mortise.

11. The device according to claim 8, wherein said preload member further comprises at least one preload screw and one locking screw.

12. The device according to claim 8, wherein said preload member preloads and locks the movement of one plate relative to another.

13. The device according to claim 1, wherein the micrometer screw is a press fit.

14. The device according to claim 1, wherein the bracket is rectangular.

15. A device for positioning an object in space, comprising at least four plates, each one of said plates is contiguous with and capable of adjustment with respect to at least one other plate of the at least four plates, wherein at least a first one of the plates is contiguous with a second one of the plates, and the first and second plates further comprise:
   at least one tenon/mortise assembly, wherein the tenon/mortise assembly includes at least a first interface having at least a first tenon and a first mortise and a second interface having at least a second tenon, wherein the second tenon is configured to fit inside the first mortise;
   a preload, in contact with a first portion of the first mortise, for limiting the movement of the second tenon inside the first mortise by preloading the first portion of the first mortise toward the second tenon;
   an adjusting mechanism for adjusting the relation of the first plate with respect to the second plate, wherein the adjusting mechanism comprises:
      a micrometer screw secured to at least one of the first and second plate;
      a collar surrounding a first end of the micrometer screw;
      a bracket having an opening corresponding to an outside diameter of a body of the collar, wherein the collar and micrometer screw pass through the opening in the bracket.

16. The device of claim 15, wherein the first portion of the first mortise is a blade having a distal end and a proximal end that is narrower than the distal end, wherein the distal end is preloaded toward the second tenon by the preload.

17. The device according to claim 15, wherein the preload further comprises at least one preload screw and one locking screw, wherein the locking screw preloads and locks the movement of one plate relative to another.

18. A device for positioning an object in space, comprising at least four plates, each one of said plates is contiguous with and capable of adjustment with respect to at least one other plate of the at least four plates, wherein at least a first one of the plates is contiguous with a second one of the plates, and the first and second plates further comprise:
   at least one tenon/mortise assembly, wherein the tenon/mortise assembly includes at least a first interface having at least a first tenon and a first mortise and a second interface having at least a second tenon configured to fit inside the first mortise, wherein the first mortise has a blade that exhibits a lateral elasticity, the blade having a distal end and a proximal end, wherein the blade is formed as a unitary structure with one of the first and second plates;

a threaded preload, in contact with the blade, for limiting the movement of the second tenon inside the first mortise by preloading the blade toward the second tenon;

an adjusting mechanism for adjusting the relation of the first plate with respect to the second plate, wherein the adjusting mechanism comprises:

a micrometer screw secured to at least one of the first and second plate, wherein the micrometer screw is threaded into at least one of the first plate and the second plate.

19. The device of claim 18, wherein the adjusting mechanism further comprises:

a collar surrounding a first end of the micrometer screw;

a bracket having an opening corresponding to the outside diameter of the collar, wherein the collar and micrometer screw passes through the opening in the bracket.

20. The device according to claim 18, wherein the preload further comprises at least one locking screw, wherein the locking screw preloads and locks the movement of one plate relative to another.

\* \* \* \* \*